US 6,746,486 B1

(12) United States Patent
Shultz et al.

(10) Patent No.: US 6,746,486 B1
(45) Date of Patent: Jun. 8, 2004

(54) METHOD AND APPARATUS FOR TOTAL WRIST ANGLED BACK CARPAL PLATE

(75) Inventors: Jason M. Shultz, Warsaw, IN (US); Andrew K. Palmer, Cazenovia, NY (US); Kevin T. Stone, Winona Lake, IN (US)

(73) Assignee: Biomet, Inc., Warsaw, IN (US)

( * ) Notice: Subject to any disclaimer, the term of this patent is extended or adjusted under 35 U.S.C. 154(b) by 0 days.

(21) Appl. No.: 10/279,240

(22) Filed: Oct. 24, 2002

(51) Int. Cl.$^7$ .................................................. A61F 2/42
(52) U.S. Cl. .................................................. 623/21.12
(58) Field of Search ........................ 623/21.11, 21.12, 623/21.13, 21.14, 21.15; 606/60, 69, 70, 71, 73, 74

(56) References Cited

U.S. PATENT DOCUMENTS

| | | | |
|---|---|---|---|
| 3,875,594 A | 4/1975 | Swanson | |
| 4,106,128 A | 8/1978 | Greewald et al. | |
| 4,158,893 A | 6/1979 | Swanson | |
| 4,164,793 A | 8/1979 | Swanson | |
| 4,178,640 A | 12/1979 | Buechler et al. | |
| 4,198,713 A | 4/1980 | Swanson | |
| 4,784,661 A | 11/1988 | Beckenbaugh et al. | |
| 4,944,757 A | * 7/1990 | Martinez et al. | ......... 623/20.15 |
| 5,314,485 A | 5/1994 | Judet | |
| 5,326,364 A | 7/1994 | Clift, Jr. et al. | |
| 5,507,821 A | 4/1996 | Sennwald et al. | |
| 5,702,470 A | * 12/1997 | Menon | ..................... 623/21.12 |
| 5,853,413 A | * 12/1998 | Carter et al. | .................. 606/69 |
| 6,059,832 A | 5/2000 | Menon | |

FOREIGN PATENT DOCUMENTS

| | | |
|---|---|---|
| EP | 0 034 192 | 8/1981 |
| WO | WO 92/00709 | 1/1992 |

OTHER PUBLICATIONS

Universal Total Wrist Implant System at www.visitkmi.com/totwrist.html.

* cited by examiner

Primary Examiner—David J. Isabella
(74) Attorney, Agent, or Firm—Harness, Dickey & Pierce, P.L.C.

(57) ABSTRACT

A prosthetic wrist having a radial insert, which is configured to be fixed to the resected radius of a patient, a carpal implant and a wrist bearing component. The carpal implant includes a body and a pair of flanges, each of which being skewed to the axis of the body in a manner that permits them to abut the ulnar side of the hamate bone and the radial side of the distal portion of the carpal bone complex, respectively. The wrist bearing component may include a bearing surface for contacting the radial insert that is defined by different radii in the coronal and sagittal planes and an alignment mechanism may be employed to fix the wrist bearing component in a desired orientation.

39 Claims, 9 Drawing Sheets

METHOD AND APPARATUS FOR TOTAL WRIST ANGLED BACK CARPAL PLATE

FIELD OF THE INVENTION

The present invention generally relates to prosthetic implants and more particularly to a prosthetic wrist implant having a geometry that closely matches that of a natural wrist, which is adjustable during the implantation process so as to more closely approximate the motion of a natural wrist, and which achieves good stability through better apposition and compression with the remaining carpal bones.

BACKGROUND OF THE INVENTION

Figure 1:
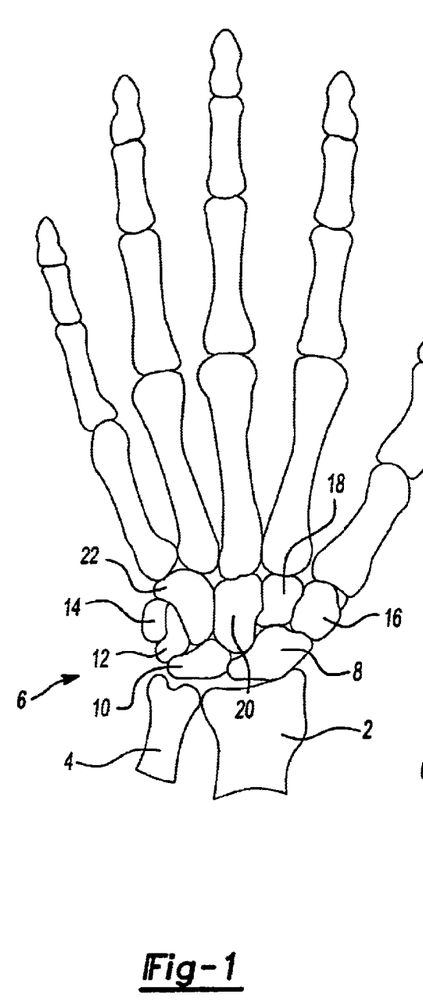
FIG. 1 is a view of the dorsal side of a patient's left hand and wrist illustrating the bone structure of the hand and wrist in conjunction with the radius and the ulna.

With reference to FIG. 1 of the drawings, the dorsal side of the bone structure of a patient's left hand and wrist is illustrated in conjunction with the radius 2 and the ulna 4. The bone structure includes a carpal bone complex 6 having a scaphoid 8, a lunate 10, a triquetrum 12, a pisiform 14, a trapezium 16, a trapezoid 18, a capitate 20 and a hamate 22. It will be appreciated that the scaphoid 8 and the lunate 10 bones articulate with the radius 2 during the movement of the wrist.

In a variety of wrist disorders, patients may experience discomfort, pain and difficulty in moving the wrist. Prior surgical treatment of this condition involved fusion to inhibit movement of the scaphoid 8 and the lunate 10 bones relative to the radius to thereby alleviate pain in the patient's wrist. This procedure, however, leaves the patient without motion in their wrist and thereby severely restricts the use of their wrist. Modernly, prosthetic wrist implants have been developed to provide a pair of artificial bearing surfaces for the wrist. Several of the prior wrist implants have suffered from drawbacks including limited range of motion and excessive bone resection. Others still provide proper motion only when aligned in an extremely precise manner relative to the carpal bone complex 6. While various jigs and fixtures may be employed to aid in the locating and forming of a hole in the distal portion of the carpal bone complex 6 for receiving a carpal implant, these devices typically do not completely eliminate the possibility of error in the alignment and forming of the hole.

Accordingly, there remains a need in the art for an improved prosthetic wrist implant that provides improved support and strength for the distal portion of the carpal bone complex 6 and which has a bearing surface whose orientation is changeable after implantation to provide the implanted prosthetic wrist with a range of motion that mimics the range of motion of a natural wrist.

SUMMARY OF THE INVENTION

In one form, the present invention provides a prosthetic wrist with a carpal implant that includes a body, a lateral flange and a medial flange. The body has a stem that is arranged along an axis and which is configured to be implanted in a capitate bone in a human wrist. The lateral flange, which includes a lateral bone abutment surface that is configured to be abutted against an ulnar side of a hamate bone in the human wrist, is coupled to the body and extends therefrom such that at least a portion of the lateral bone abutment surface is skewed to the axis of the stem by an angle of less than 90 degrees. The medial flange, which has a medial bone abutment surface that is configured to abut against a radial side of a trapezium bone and a portion of a resected scaphoid bone of the human wrist, is coupled to the body and extends therefrom on a side opposite the lateral flange.

In another form, the present invention provides a method for implanting a prosthetic wrist implant between a patient's radius and carpal bone complex. The method includes: providing a carpal implant including a body, a lateral flange and a medial flange, the body having a stem that is arranged along an axis, the lateral flange being coupled to the body and extending therefrom, the lateral flange having a lateral bone abutment surface, at least a portion of the lateral bone abutment surface being skewed to the axis of the stem by an angle of less than 90 degrees, the medial flange being coupled to the body and extending therefrom on a side opposite the lateral flange, the medial flange having a medial bone abutment surface that is skewed to the axis of the stem by an angle of less than 90 degrees, each of the lateral and medial flanges having a bone screw aperture formed therethrough; resectioning a proximal portion of the carpal bone complex; forming an opening in the capitate bone that lies along an axis that is generally coincident with the axis of the capitate bone; forming a pair of securing apertures into a distal portion of the carpal bone complex, one of the pair of securing apertures being formed in the hamate bone; securing the carpal implant to the distal portion of the carpal bone complex such that the stem is at least partially disposed in the opening in the capitate bone and engaged to the capitate; providing a first screw and a second screw, the first and second screws being appropriately sized to the pair of securing apertures and the bone screw apertures; placing the first screw through the bone screw aperture in the lateral flange and the securing aperture in the hamate bone and securing the first screw to the hamate to bring the lateral bone abutment surface into abutment with an ulnar side of a hamate bone; and placing the second screw through the bone screw aperture in the medial flange and the other securing aperture in the distal portion of the carpal bone complex and securing the second screw to the distal portion of the carpal bone complex to bring the medial bone abutment surface into abutment with a radial side of the distal portion of the carpal bone complex.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Additional advantages and features of the present invention will become apparent from the subsequent description and the appended claims, taken in conjunction with the accompanying drawings, wherein:

DETAILED DESCRIPTION OF THE PREFERRED EMBODIMENTS

Figure 2:
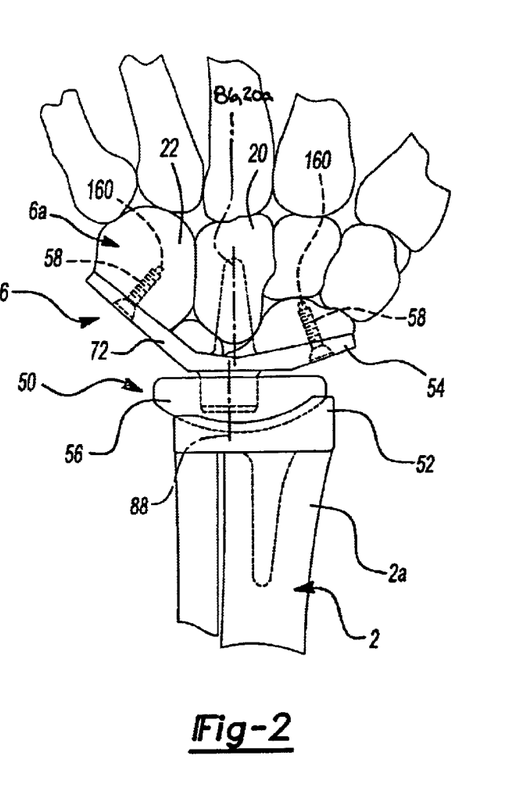
FIG. 2 is a view of the dorsal side of a patient's left hand and wrist illustrating the implantation of a prosthetic wrist implant constructed in accordance with the teachings of the present invention.
Figures 3, 4:
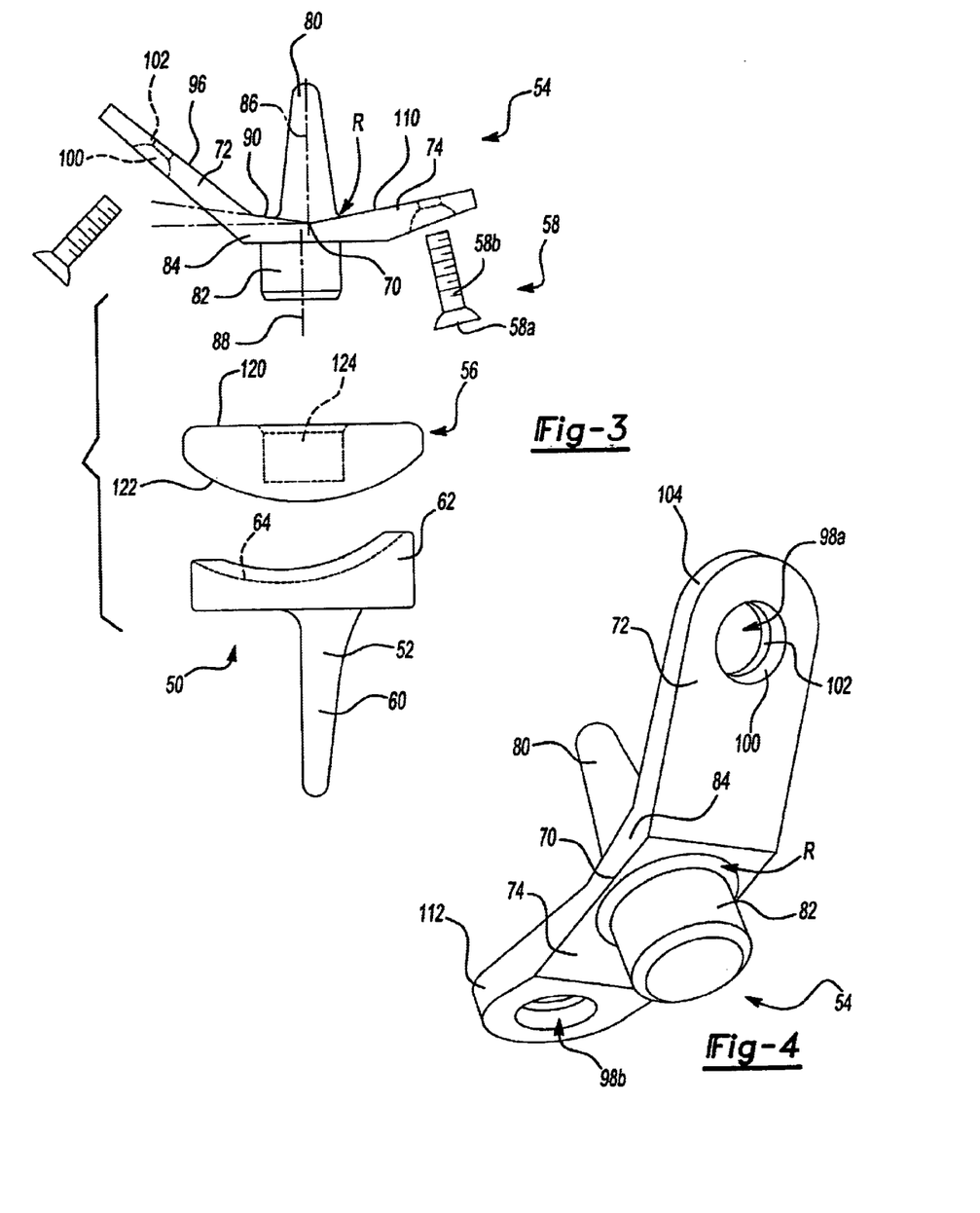
FIG. 3 is an exploded view of a prosthetic wrist constructed in accordance with the teachings of the present invention.
FIG. 4 is a perspective view of a portion of the prosthetic wrist of FIG. 2 illustrating the carpal implant in greater detail.

With reference to FIGS. 2 and 3 of the drawings, a prosthetic wrist constructed in accordance with the teachings of the present invention is generally indicated by reference numeral 50. The prosthetic wrist 50 is illustrated in a post operative condition as implanted to a distal portion 2a of the radius 2 and a distal portion 6a of the carpal bone complex 6. As those skilled in the art will appreciate, the distal portion 2a of the radius 2 and the distal portion 6a of the carpal bone complex 6 are formed when the surgeon resects a portion of the radius 2 and the carpal bone complex 6 from the patient prior to implantation of the prosthetic wrist 50.

The prosthetic wrist is illustrated to include a radial implant 52, a carpal implant 54, a wrist bearing component 56 and a plurality of conventional bone screws 58. The radial implant 52 includes a radial stem 60, which is configured to be implanted into a distal portion 2a of the radius 2, and a bearing guide 62, which is fixed to the distal end of the radial stem 60. The bearing guide 62 includes a bearing or concave guide surface 64 that is configured to engage in a mating manner the wrist bearing component 56. In the preferred embodiment, the radial implant 52 is unitarily formed from a titanium material, such as Ti-6AI-4V (F136), although those skilled in the art will understand that other materials having sufficient strength and biocompatibility may also be employed. Those skilled in the art will also understand that the radial implant 52 may be configured in a modular manner, wherein the radial stem 60 and the bearing guide 62 are discrete elements that are coupled together prior to or during the process of implementation.

With additional reference to FIGS. 3 and 4, the carpal implant 54 is illustrated to include a body 70, a lateral flange 72 and a medial flange 74. The carpal implant 54 is unitarily formed from a titanium material, such as Ti-6AI-4V (F136), although those skilled in the art will understand that other materials having sufficient strength and biocompatibility may also be employed.

The body 70 includes a stem 80, a proximal stem 82 and an interconnecting flange 84. The stem 80, which is formed along a stem axis 86 and extends from the distal side of the body 70, is configured to be inserted into a hole formed in the capitate 20 (FIG. 2) so that the stem axis 86 will extend generally parallel an axis 20a of the capitate 20 when the body 70 is implanted. The proximal stem 82 extends in a direction opposite the stem 80 and is sized to engage the wrist bearing component 56. In the particular embodiment illustrated, the proximal stem 82 is formed as a tapered cylinder having an axis 88 that is offset laterally from the stem axis 86. Those skilled in the art will appreciate, however, that the axis 88 of the proximal stem 82 may be coincident with the stem axis 86. The taper of the proximal stem 82 is configured to the profile of a conventional Morse taper for attachment to the wrist bearing component 56. A fillet radius R is employed to reduce the concentration of stress at the points at which the stem 80 and the proximal stem 82 are joined to the remainder of the body 70.

The interconnecting flange 84 couples the stem 80 to the lateral flange 72. The interconnecting flange 84 includes an interconnecting bone abutment surface 90 that is skewed to the stem axis 86 by an angle that is less than 90 degrees in magnitude and which is preferably about 80 degrees to permit the interconnecting flange 84 to conform to the proximal end of the distal portion 6a of the carpal bone complex 6.

The lateral flange 72 is coupled to a side of the interconnecting flange 84 proximate the stem 80 and has a lateral bone abutment surface 96 that is configured to abut an ulnar side of the hamate 22 and which projects upwardly from the body 70 in a manner that is skewed to both the stem axis 86 and the interconnecting bone abutment surface 90 by an angle of less than 90 degrees. A securing aperture 98*a*, which is formed in the distal end of the lateral flange 72 along an axis that is generally perpendicular to the lateral bone abutment surface 96, is illustrated to include a first portion 100 and a second portion 102. The first portion 100 of the securing aperture 98*a* has a spherical shape that is configured to matingly engage the frusto-conical surface of the head 58*a* of a bone screw 58. (FIG. 3). The second portion 102 of the securing aperture 98*a* has a generally cylindrical shape that is sized to receive the body 58*b* of the bone screw 58.

In the particular embodiment illustrated, the lateral bone abutment surface 96 is arranged at an angle of about 50 degrees relative to the stem axis 86. The distal end of the lateral flange 72 terminates at an arcuate edge 104 that is defined by a radius that is centered at the centerpoint of the securing aperture 98*a*. As those skilled in the art will readily appreciate, however, the center of the radius need not be centered at the centerpoint of the securing aperture 98*a*.

The medial flange 74 is coupled to the body 70, and more specifically to the interconnecting flange 84, on a side opposite the lateral flange 72 and includes a medial bone abutment surface 110 that is configured to abut a radial side of the distal portion 6*a* of the carpal bone complex 6 and which projects upwardly from the body 70 in a manner that is skewed to the stem axis 86 by an angle of less than 90 degrees. In the particular embodiment illustrated, the medial bone abutment surface 110 is skewed to the stem axis 86 by an angle of about 80 degrees. Like the lateral flange 72, the medial flange 74 includes a securing aperture 98*b* and terminates at its distal end at an arcuate edge 112 that is defined by a radius that is centered at the centerpoint of the securing aperture 98*b*. The securing aperture 98*b* is substantially identical to the securing aperture 98*a* but is formed about an axis that is generally perpendicular to the medial bone abutment surface 110.

In view of the above discussion, those skilled in the art will appreciate that one general concept of the present invention is the provision of a carpal implant having medial and lateral flanges that are configured to abut portions of the carpal bone complex (whether resected or not) in a way that supports the bones of the medial and lateral sides of the carpal bone complex. Accordingly, those skilled in the art will appreciate that the carpal implant of the present invention may be formed in any generally concave manner (i.e., wherein at least a portion of each of the medial and lateral flanges is skewed to the axis of the body) that is configured to abut the medial and lateral sides of the carpal bone complex (whether resected or not). Other examples of the "concave" formation of the carpal implant of the present invention are illustrated in FIGS. 10 through 12 and 15 through 27 and will be described in detail below.

Figure 5:
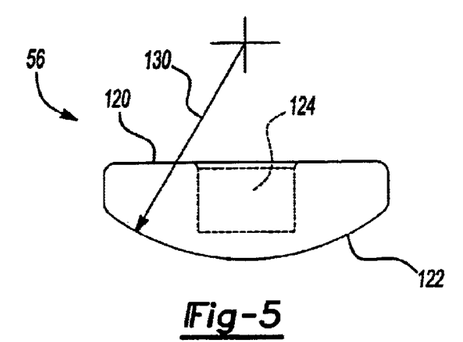
FIG. 5 is a side view of a portion of the prosthetic wrist of FIG. 2 illustrating the wrist bearing component in the coronal plane.
Figure 6:
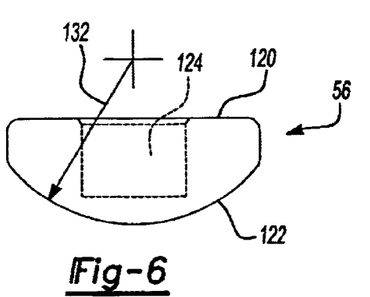
FIG. 6 is a side view of a portion of the prosthetic wrist of FIG. 2 illustrating the wrist bearing component in the sagittal plane.

With renewed reference to FIGS. 2 and 3 and additional reference to FIGS. 5 and 6, the wrist bearing component 56 has the general shape of an ellipsoidal segment and includes a generally flat abutting edge 120 and a wrist bearing surface 122. As those skilled in the art will appreciate, the wrist bearing surface 122 does not extend to a point where it intersects the abutting edge 120 as this would cause the wrist bearing component 56 to be too large in size. Accordingly, the flat sides at which the wrist bearing surface 122 terminates permit the wrist bearing surface 122 to be shaped in a desired manner while maintaining proper sizing of the wrist bearing component 56. A securing feature 124 is formed into or otherwise coupled to the abutting edge 120 to permit the wrist bearing component 56 to be secured to the proximal end of the carpal implant 54. In the particular example provided, the securing feature 124 is a blind tapered hole that is configured to matingly engage the proximal stem 82. Those skilled in the art will readily understand, however, that any appropriate coupling means may be employed to couple the wrist bearing component 56 to the carpal implant 54 and as such, the scope of the present invention will not be so limited as to require the coupling of the wrist bearing component 56 and the carpal implant 54 through the engagement of a tapered stem with a tapered hole. As those skilled in the art will appreciate, the modular nature of the wrist bearing component 56 permits the surgeon to select from a variety of wrist bearing components 56 that are differently sized and/or shaped to permit the surgeon to tailor the prosthetic wrist 50 to the individual needs of the patient. Those skilled in the art will also appreciate that the surgeon's selection of a particular wrist bearing component 56 may necessitate the use of a particular radial implant 52 that has a correspondingly different size and/or configuration.

The wrist bearing component 56 is preferably formed from a cobalt chromium alloy, such as CoCrMo, which provides fatigue and corrosion resistance, as well as a relatively high degree of strength. Those skilled in the art will understand that other appropriate materials, including metals and/or plastics, may alternatively be employed to form the wrist bearing component 56 or a portion thereof which includes the wrist bearing surface 122.

With particular reference to FIGS. 5 and 6, the wrist bearing surface 122 is illustrated as being defined by a first radius 130 in the coronal plane and a second radius 132 in the sagittal plane. Preferably, the first and second radii 130 and 132 are different and more preferably, the first radius 130 is larger than the second radius 132. Configuration of the wrist bearing component 56 in this manner permits the prosthetic wrist 50 to move in a manner that more closely approximates the motion of a natural wrist.

Figure 7:
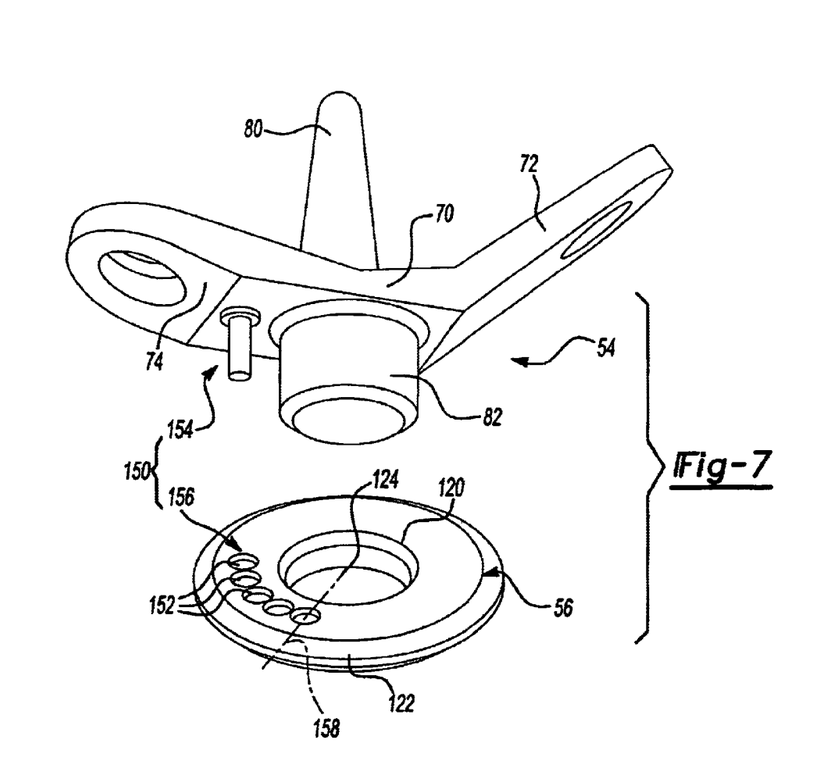
FIG. 7 is an exploded perspective view of a prosthetic wrist similar to that of FIG. 2 but additionally including an alignment mechanism for radially fixing the wrist bearing component relative to the carpal implant.

In situations where the wrist bearing surface 122 is contoured in a manner that is not defined by a single spherical radius, the orientation of the wrist bearing component 56 relative to the radial implant 52 is critical. Accordingly, the prosthetic wrist 50 preferably also includes an alignment mechanism 150 in such situations for radially fixing the wrist bearing component 56 relative to the carpal implant 54 as is illustrated in FIG. 7. Preferably, the alignment mechanism 150 permits the surgeon implanting the prosthetic wrist 50 to orient the wrist bearing surface 122 to a predetermined installation orientation that is dependent upon the orientation between the implanted carpal implant 54 and the implanted radial implant 52. For example, if the radial implant 52 were to be fixed to the distal portion 2*a* of the radius 2 in a manner that was rotated slightly from that which was considered "nominal", the surgeon may be able to compensate for the slight radial offset by rotating the wrist bearing component 56 relative to the carpal implant 54 in an equivalent manner.

The alignment mechanism 150 may permit the wrist bearing component 56 to be rotated in an infinite number of positions relative to the carpal implant 54, as would the connection of the wrist bearing component 56 to the carpal implant 54 through the Morse taper connection of the proximal stem 82 and the blind tapered hole of the securing feature 124, or through adhesives, or recessed screws that extend through the wrist bearing component 56 and which engage the body 70 of the carpal implant 54.

In the particular example provided, the alignment mechanism 150 permits the wrist bearing component 56 to be rotated into one of a plurality of predetermined orientations 152. In this regard, the alignment mechanism 150 is illustrated to include a coupling member 154, which is coupled to the carpal implant 54, and a plurality of holes 156 that are formed into the wrist bearing component 56. Each of the holes 156 is sized to receive the coupling member 154 and is defined by a centerline 158 that is spaced circumferentially apart from the centerline 158 of an adjacent hole 156. Rotation of the wrist bearing component 56 relative to the carpal implant 54 is accomplished via engagement of the coupling member 154 into an associated one of the holes 156 that permits the wrist bearing component 56 to be placed in the installation orientation relative to the radial implant 52. Those skilled in the art will understand that the coupling member 154 may be removably coupled to the carpal implant 54 so as to provide the surgeon with an option not to use the coupling member 154 should the surgeon need more flexibility in positioning the wrist bearing component 56 relative to the carpal implant 54. Those skilled in the art will also understand that the coupling member 154 and the holes 156 may be reversed (i.e., the coupling member 154 may be attached to the wrist bearing component 56 and the holes 156 may be formed in the carpal implant 54).

In another preferred form, the present invention provides a method for implanting a prosthetic wrist 50 between the radius 2 and the portion 6a of the carpal bone complex 6 of a patient. The method includes: providing a carpal implant 54 including a body 70, a lateral flange 72 and a medial flange 74, the body 70 having a stem 80 that is arranged along an axis 86, the lateral flange 72 being coupled to the body 70 and extending therefrom, the lateral flange 72 having a lateral bone abutment surface 96, at least a portion of the lateral bone abutment surface 96 being skewed to the axis 86 of the stem 80 by an angle of less than 90 degrees, the medial flange 74 being coupled to the body and extending therefrom on a side opposite the lateral flange 72, the medial flange 74 having a medial bone abutment surface 110, each of the lateral and medial flanges 72 and 74 having a bone screw aperture 98a, 98b, respectively, formed therethrough; resectioning the carpal bone complex 6 along lines that are skewed to an axis of the capitate 20 and which correspond to the distal faces of the lateral and medial flanges 72 and 74 and the interconnecting flange 84; forming an opening in the capitate 20 that lies along an axis that is generally coincident with the axis of the capitate 20; forming a pair of securing apertures 160 (FIG. 2) into the distal portion 6a of the carpal bone complex 6, one of the pair of securing apertures 160 being formed in the hamate 22; securing the carpal implant 54 to the distal portion 6a of the carpal bone complex 6 such that the stem 80 is at least partially disposed in the opening in the capitate 20 and engaged to the capitate 20; providing a first and second screws 58, the first and second screws 58 being appropriately sized to the pair of securing apertures 160 and the bone screw apertures 98a, 98b; placing the first screw through the bone screw aperture 98a in the lateral flange 72 and the securing aperture 160 in the hamate 22 and securing the first screw to the hamate 22 to bring the lateral bone abutment surface 96 into abutment with an ulnar side of a hamate 22; and placing the second screw 58 through the bone screw aperture 98b in the medial flange 74 and the other securing aperture 160 in the distal portion 6a of the carpal bone complex 6 and securing the second screw 58 to the distal portion 6a of the carpal bone complex 6 to bring the medial bone abutment surface 110 into abutment with a radial side of the distal portion 6a of the carpal bone complex 6.

Preferably, the method also includes: providing a wrist bearing component 56 having a wrist bearing surface 122 that is defined by a first radius 130 in the coronal plane and a second, different radius 132 in the sagittal plane; coupling the wrist bearing component 56 to a proximal stem 82 formed on the body 70 of the carpal implant 54 such that the wrist bearing component 56 is rotatable relative to the carpal implant 54; and fixing the wrist bearing component 56 to the proximal stem 82 such that the wrist bearing component 56 is aligned at a predetermined installation orientation relative to the distal portion 6a of the carpal bone complex 6.

Figure 8:
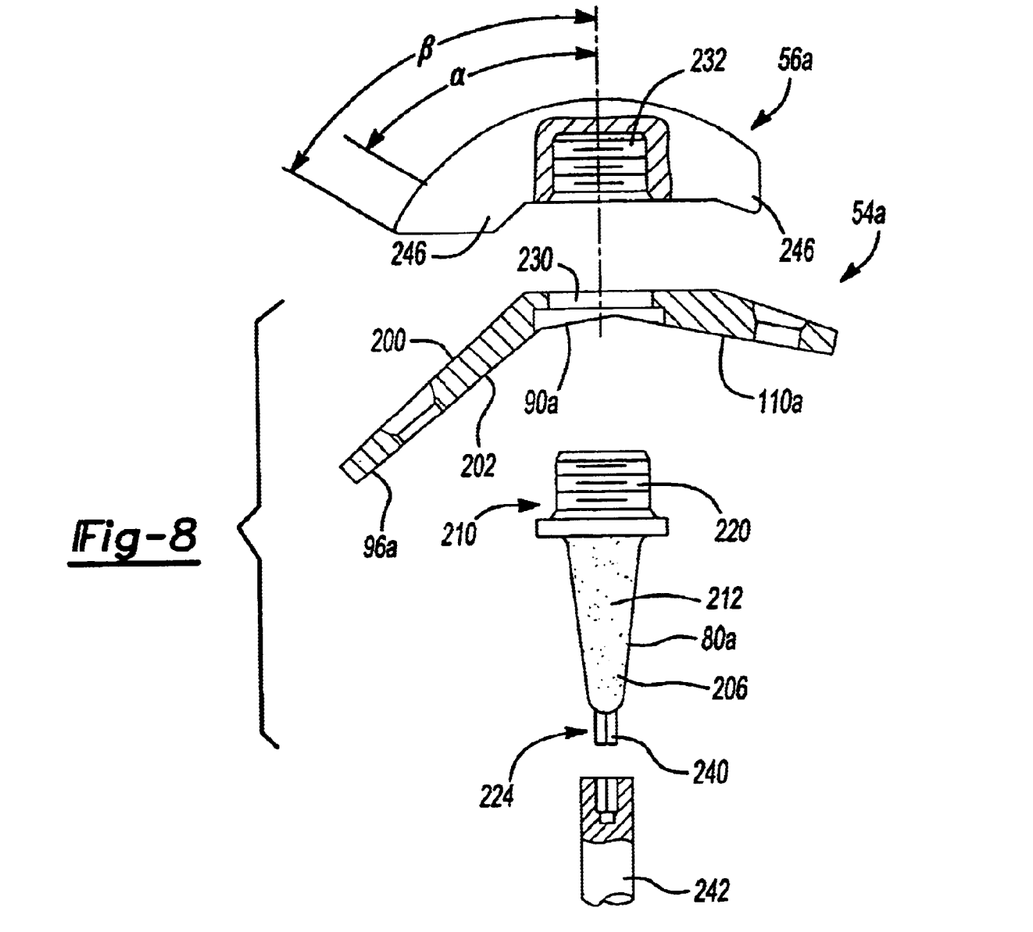
FIG. 8 is an exploded view in partial section of a prosthetic wrist constructed in accordance with the teachings of a second embodiment of the present invention.

While the carpal implant 54 has been described thus far as being unitarily formed and used in conjunction with a discrete wrist bearing component 56, those skilled in the art will appreciate that the invention, in its broader aspects, may be constructed somewhat differently. For example, the carpal implant 54a may be configured to include a discrete flange structure 200 and a discrete stem 80a as illustrated in FIG. 8. The flange structure 200 is unitarily formed from a suitable material, such as CoCrMo, and includes a bone abutment surface 202. In the particular example provided, the bone abutment surface 202 is shown to include an interconnecting, lateral and medial bone abutment surfaces 90a, 96a and 110a, respectively, which mimic the configurations of the interconnecting, lateral and medial bone abutment surfaces 90, 96, 110 (FIG. 3), respectively.

The stem 80a is illustrated to include a tapered cylindrical portion 206, which is configured to be fitted to a hole that is formed in the capitate 20 (FIG. 2), and a connecting portion 210 for coupling the stem 80a to the flange structure 200. The tapered cylindrical portion 206 is generally similar to the stem 80 (FIG. 3) discussed above and includes a porous coating 212.

In the example provided, the connecting portion 210 includes a threaded end portion 220, which is coupled to a proximal end of the tapered cylindrical portion 206, and a driving portion 224, which is coupled to an end of the tapered cylindrical portion 206 opposite the threaded end portion 220. The threaded end portion 220 is configured to extend through a stem receiving aperture 230 that is formed in the flange structure 200 and threadably engage a threaded aperture 232 that is formed in the wrist bearing component 56a. The driving portion 224 is illustrated to include a geometric feature, such as a male hexagon shank 240, that permits the stem 80a to be rotated with an appropriately configured tool 242 such that the threaded end portion 220 threadably engages the threaded aperture 232 in the wrist bearing component 56a. Those skilled in the art will readily understand that the driving portion 224 may be of any shape (e.g., triangular, square, Torx®) and may extend from the tapered cylindrical portion 206 in the form of a shank, or be recessed into the tapered cylindrical portion 206, in which case the tool 242 would have a corresponding male end to engage the driving portion 224, rather than a corresponding female as illustrated in this example.

With the exception of the threaded aperture 232 and a pair of anti-rotation tabs 246, the wrist bearing component 56a is otherwise identical to the wrist bearing component 56 of FIG. 2. The anti-rotation tabs 246 are configured to abut a proximal side of the flange structure 200 when the wrist bearing component 56a is coupled to the carpal implant 54a to thereby inhibit relative rotation between the wrist bearing component 56a and the carpal implant 54a. Those skilled in the art will appreciate, however, that other anti-rotation means may additionally or alternatively be incorporated into wrist bearing component 56a and/or the carpal implant 54a, including mating geometric features (e.g., a male hex protrusion formed onto the proximal side of the flange structure 200 and a mating hex recess formed into the distal side of the wrist bearing component 56*a*), fasteners and pins. The use of anti-rotation tabs 246 provides the wrist bearing component 56 with a relatively greater range of motion as comparatively illustrated by the angles α and β.

Figure 9:
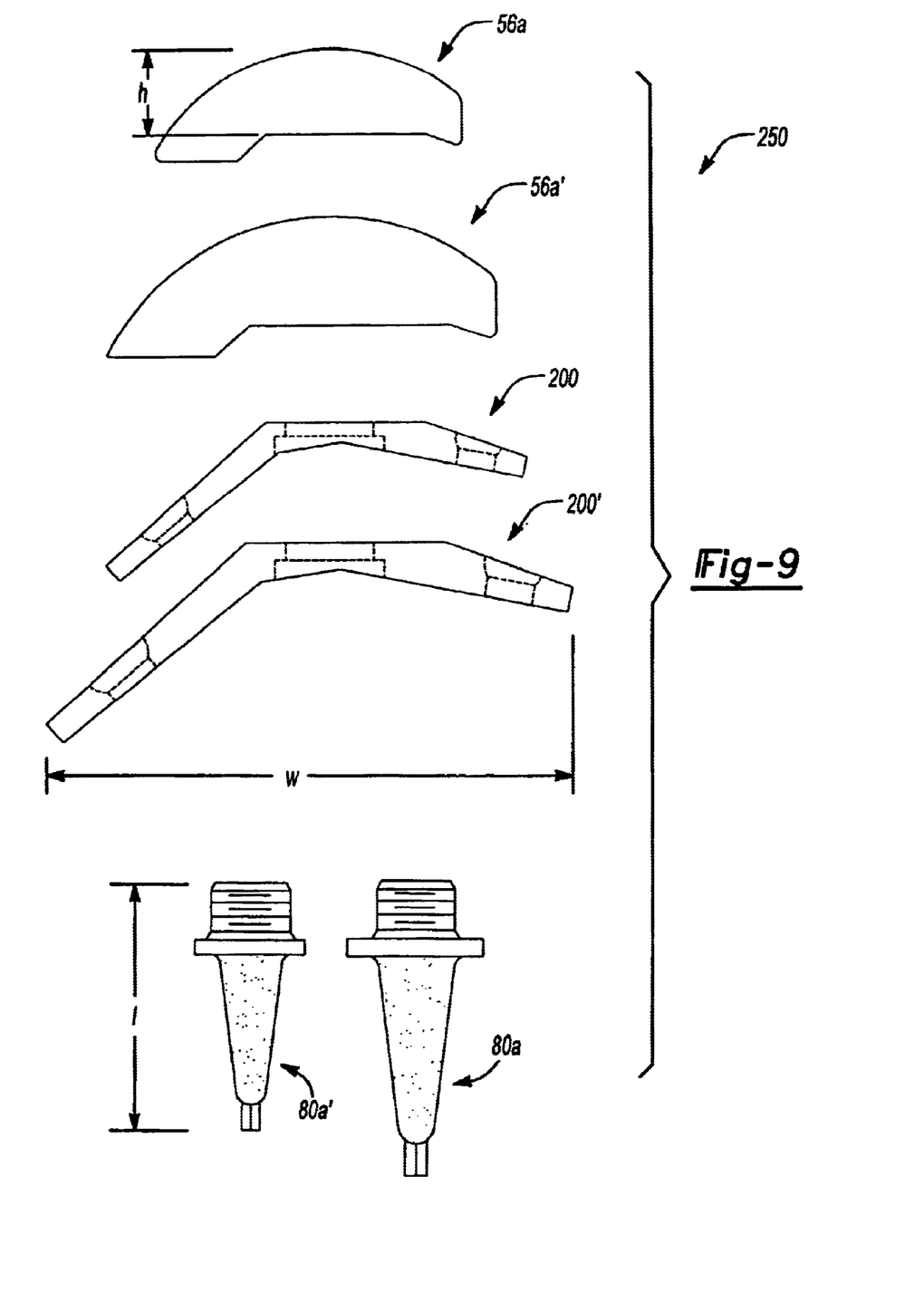
FIG. 9 is a view of a kit that utilizes the prosthetic wrist of FIG. 8.

The modular configuration described above provides the surgeon with a relatively high degree of flexibility when differently sized components are available in a kit form as shown in FIG. 9. In the example illustrated, several wrist bearing components (i.e., wrist bearing components 56*a* and 56*a*'), several flanges (i.e., flanges 200 and 200') and several stems (i.e., stems 80*a* and 80*a*') are provided in a kit 250. The wrist bearing components 56*a* and 56*a*' are configured with an identical articular shape, but vary in their overall height dimension h. Similarly, the flanges 200 and 200' and stems 80*a* and 80*a*' are similarly configured, but vary proportionally to achieve a desired overall width, w, and/or length, l, for example.

Figure 10:
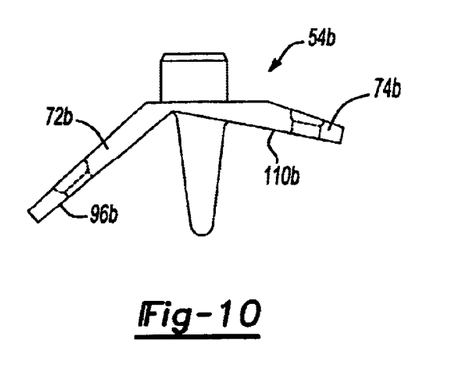
FIG. 10 is a side elevation view of a carpal implant constructed in accordance with the teachings of a third embodiment of the present invention.
Figure 11:
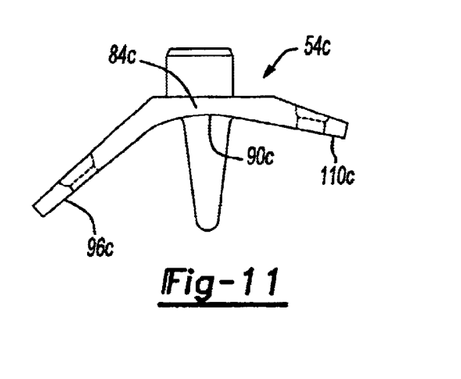
FIG. 11 is a side elevation view of a carpal implant constructed in accordance with the teachings of a fourth embodiment of the present invention.

In the embodiments of FIGS. 10 and 11, the carpal implants 54*b* and 54*c* are generally similar to the carpal implant 54 (FIG. 3), except for the configuration of the interconnecting, lateral and medial flanges. In FIG. 10, the lateral and medial flanges 72*b* and 74*b*, respectively, intersect one another and as such, this embodiment lacks the interconnecting flange 84 of the carpal implant 54. The lateral flange 72*b* is shown to be configured such that the lateral bone abutment surface 96*b* is skewed to the stem axis 86 by an angle of about 30 degrees, while the medial flange 74*b* is shown to be configured such that the medial bone abutment surface 110*b* is skewed to the stem axis 86 by an angle of about 45 degrees. In FIG. 11, the interconnecting flange 84*c* is configured such that the interconnecting bone abutment surface 90*c* is arcuately shaped. In the particular example provided, the interconnecting bone abutment surface 90*c* is tangent to the lateral and medial bone abutment surfaces 96*c* and 110*c*, respectively.

Figures 12, 13, 14:
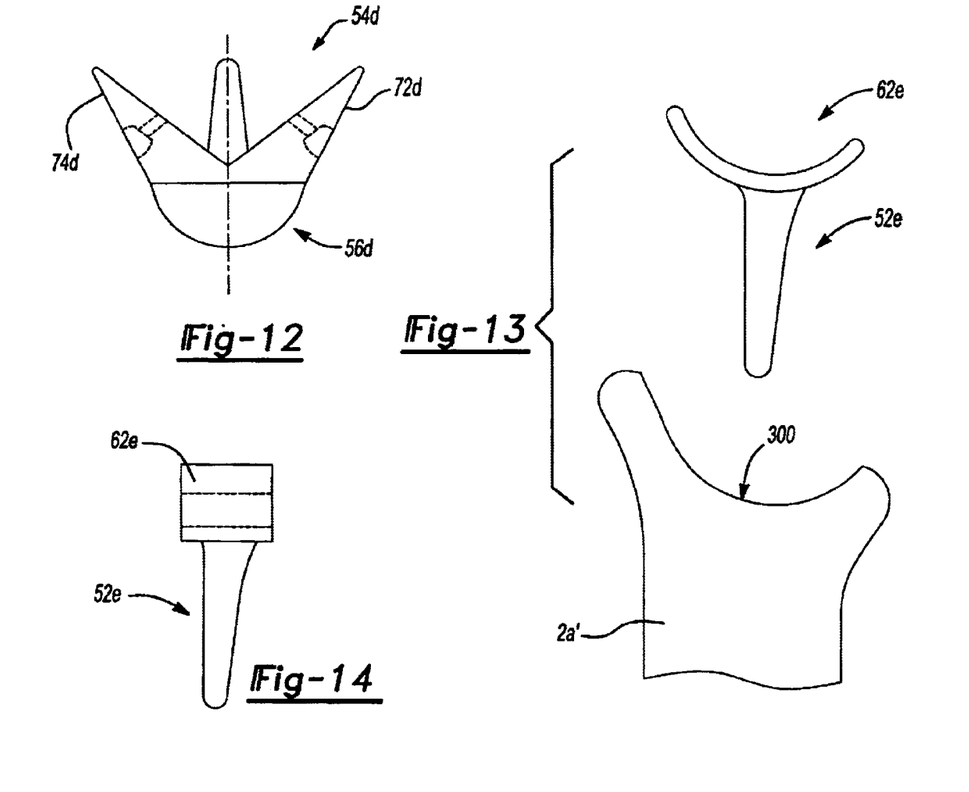
FIG. 12 is a side elevation view of a carpal implant constructed in accordance with the teachings of a fifth embodiment of the present invention.
FIG. 13 is an exploded front elevation view of a portion of a prosthetic wrist constructed in accordance with the teachings of a sixth embodiment of the present invention.
FIG. 14 is a side elevation view of a portion of the prosthetic wrist of FIG. 13.

A further embodiment is illustrated in FIG. 12, wherein the carpal implant portion 54*d* and the wrist bearing portion 56*d* are unitarily formed from a suitable material, such as CoCrMo. In the particular embodiment illustrated, the carpal implant portion 54*d* is illustrated to include lateral and medial flanges 72*d* and 74*d*, respectively, that intersect one another in a manner that is similar to the lateral and medial flanges 72*b* and 74*b*, respectively, of the carpal implant 54*b* of FIG. 10. Those skilled in the art will appreciate, however, that the lateral and medial flanges 72*d* and 74*d* may be formed differently so as to intersect at any desired angle, or such that they are spaced apart by an interconnecting portion in a manner that is similar, for example, to the configurations of the carpal implants 54 and 54*c* of FIGS. 3 and 11, respectively.

A sixth embodiment is illustrated in FIGS. 13 and 14, and illustrates an alternately constructed radial implant 52*e*, wherein the bearing guide 62*e* is formed with an arcuate shape that is configured to matingly engage the curvilinear cut 300 of a resected radius 2*a*'. Those skilled in the art will appreciate that the curvilinear cut 300 will support the bearing guide 62*e* and thereby permit the radial implant 52*e* to be formed with a relatively lower profile as compared to the radial implant 52.

Figure 15:
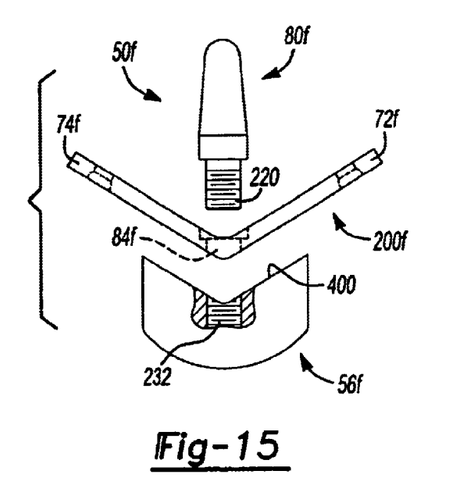
FIG. 15 is an exploded side elevation view of a prosthetic wrist constructed in accordance with the teachings of a seventh embodiment of the present invention.

A seventh embodiment is illustrated in FIG. 15, wherein the prosthetic wrist 50*f* is illustrated to be generally similar to the prosthetic wrist illustrated in FIG. 8, except for the shape of the flange structure 200*f* and the wrist bearing component 56*f*. More specifically, the flange structure 200*f* includes a generally V-shaped interconnecting flange 84*f* to which the lateral and medial flanges 72*f* and 74*f*, respectively, are oppositely coupled. As will be apparent to those skilled in the art, the wrist bearing component 56*f* is contoured to matingly engage the proximal side of the flange structure 200*f* and accordingly includes a generally V-shaped profile 400. In a manner that is similar to the prosthetic wrist of FIG. 8, the stem 80*f* includes a threaded end portion 220 that is threadably received into a threaded aperture 232 that is formed in the wrist bearing component 56*f*.

Figure 16:
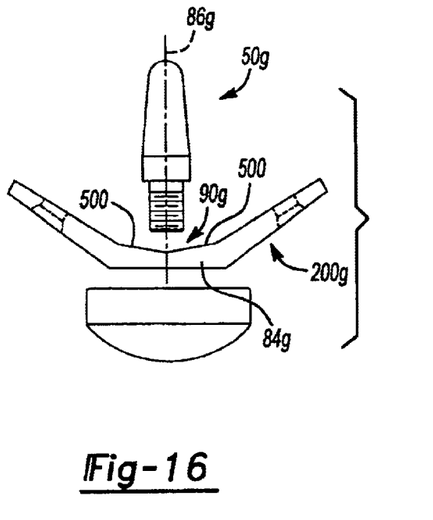
FIG. 16 is an exploded side elevation view of a prosthetic wrist constructed in accordance with the teachings of a eighth embodiment of the present invention.

An eighth embodiment is illustrated in FIG. 16, which is similar to the prosthetic wrist of FIG. 8 except for the flange structure 200*g*. The flange structure 200*g* of the prosthetic wrist 50*g* includes an interconnecting flange 84*g* with an interconnecting bone abutment surface 90*g* with a plurality of portions 500 that are each defined by a skew angle. The skew angles that define each portion 500 need not be symmetrical about the stem axis 86*g*. The skew angle of each portion 500 is less than 90 degrees in magnitude to permit the interconnecting flange 84*g* to conform and abut the proximal end of the distal portion 6*a* (FIG. 2) of the carpal bone complex 6 (FIG. 2).

Figure 17:
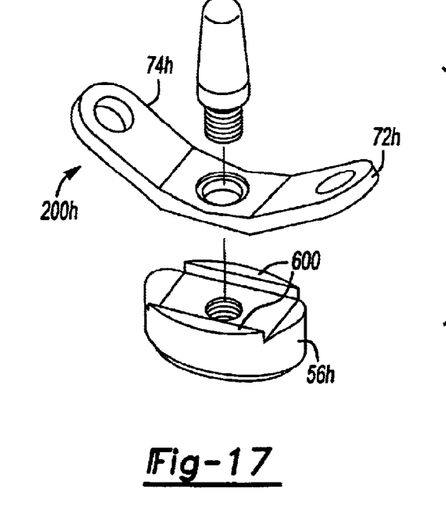
FIG. 17 is an exploded perspective view of a prosthetic wrist constructed in accordance with the teachings of a ninth embodiment of the present invention.
Figure 18:
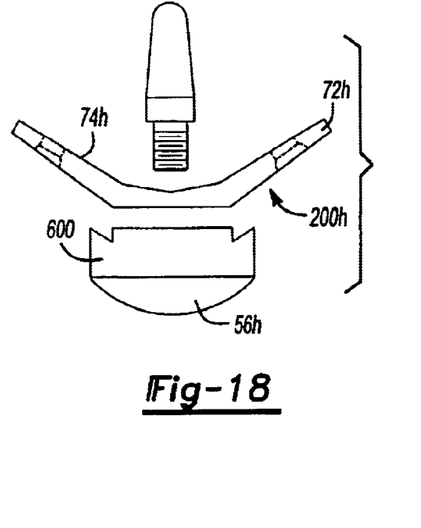
FIG. 18 is an exploded side elevation view of the prosthetic wrist of FIG. 17.

A ninth embodiment is illustrated in FIGS. 17 and 18. The flange structure 200*h* is generally identical to the flange structure 200*g* and as such, will not be discussed in further detail. The wrist bearing component 56*h* is generally similar to the wrist bearing component 56*a* (FIG. 8) in that the lateral portions of the distal side of the wrist bearing component 56*h* are angled to match the angled proximal surfaces of the lateral and medial flanges 72*h* and 74*h*, respectively. However, the wrist bearing component 56*h* also includes anterior and posterior located portions 600 on the distal sides of the wrist bearing component 56*h* that extend distally in a manner that overlaps the flange structure 200*h*. The configuration of the wrist bearing component 56*h* therefore inhibits both relative rotation and relative anterior-posterior movement between the wrist bearing component 56*h* and the flange structure 200*h*.

Figure 19:
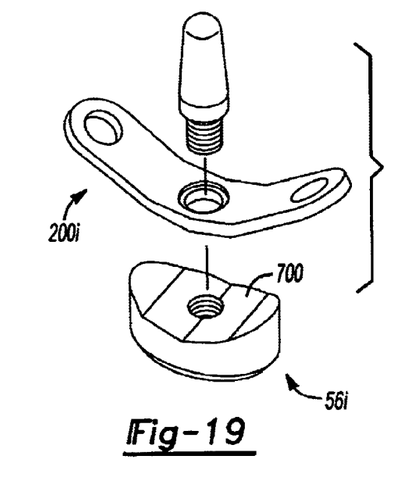
FIG. 19 is an exploded perspective view of a prosthetic wrist constructed in accordance with the teachings of a tenth embodiment of the present invention.
Figure 20:
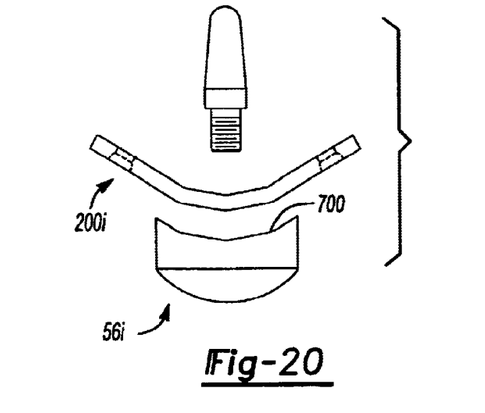
FIG. 20 is an exploded side elevation view of the prosthetic wrist of FIG. 19.

A tenth embodiment, which is also similar to the prosthetic wrist 50*g*, is illustrated in FIGS. 19 and 20. In this embodiment, the flange structure 200*i* is similar to the flange structure 200*g* except that the proximal side of the flange structure 200*i* is parallel to the distal side of the flange structure 200*i* (i.e., the proximal side of the flange structure 200*i* includes a plurality of segments that are parallel to the segments that make up the distal side of the flange structure 200*i*). As will be apparent to those skilled in the art, the wrist bearing component 56*i* is contoured to matingly engage the proximal side of the flange structure 200*i* and accordingly includes a profile 700 that matches the four angled surfaces that make up the proximal side of the flange structure 200*i*.

Figures 21, 22, 23:
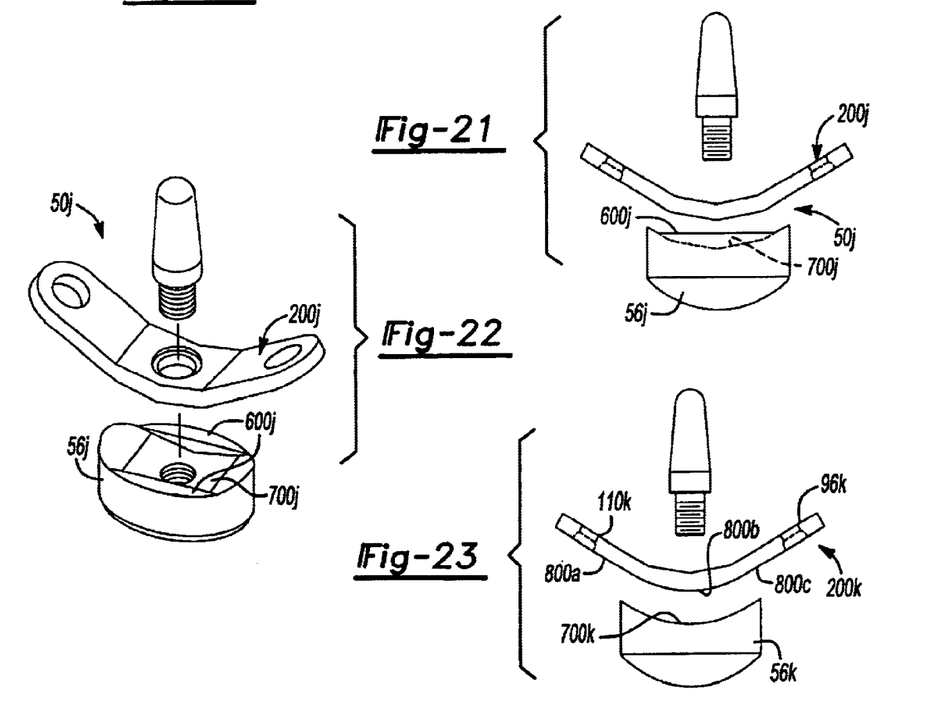
FIG. 21 is an exploded perspective view of a prosthetic wrist constructed in accordance with the teachings of an eleventh embodiment of the present invention.
FIG. 22 is an exploded side elevation view of the prosthetic wrist of FIG. 21.
FIG. 23 is an exploded side elevation view of a prosthetic wrist constructed in accordance with the teachings of a twelfth embodiment of the present invention.

An eleventh embodiment is illustrated in FIGS. 21 and 22, wherein the prosthetic wrist 50*j* is illustrated to include a flange structure 200*j* and a wrist bearing component 56*j*. The flange structure 200*j* is generally identical to the flange structure 200*i* and as such, will not be discussed in further detail. The wrist bearing component 56*j* is similar to the wrist bearing component 56*i* in that it includes a profile 700*j* that matches the four angles surfaces that make up the proximal side of the flange structure 200*j*. The wrist bearing component 56*j* also includes anterior and posterior located portions 600*j* on the distal sides of the wrist bearing component 56*j* that extend distally in a manner that overlaps the flange structure 200*j*.

A twelveth embodiment is illustrated in FIG. 23 and includes a flange structure 200*k* and a wrist bearing component 56*k*. The flange structure 200*k* includes a distal surface that is configured generally identically to the distal surface of the flange structure 200g. The proximal surface of the flange structure 200k, however, is segregated into a plurality of zones 800a, 800b and 800c. Zones 800a and 800c are generally parallel the lateral and medial bone abutment surfaces 96k and 110k. Zone 800b, which is coupled at its opposite ends to zones 800a and 800c, is defined by a radius that tangentially intersects zones 800a and 800c. The wrist bearing component 56k includes a profile 700k that matches the proximal surface of the flange structure 200k.

Figure 24:
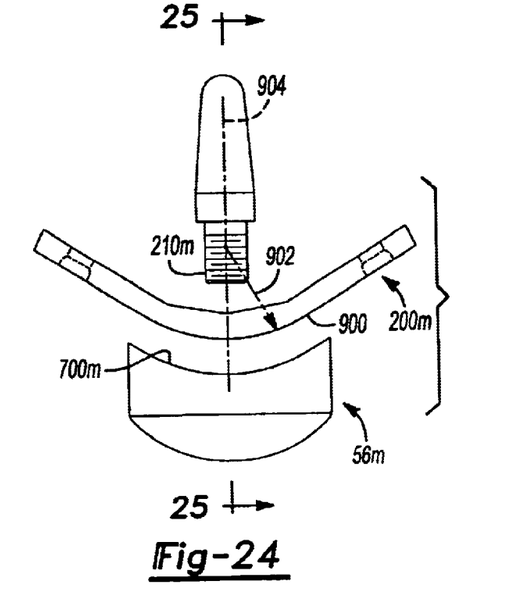
FIG. 24 is an exploded side elevation view of a prosthetic wrist constructed in accordance with the teachings of a thirteenth embodiment of the present invention.
Figure 25:
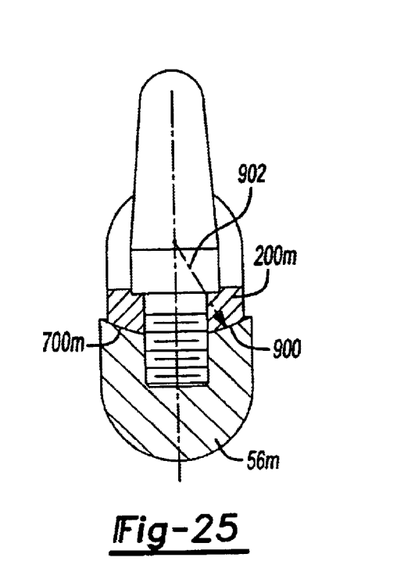
FIG. 25 is a sectional view taken along the line 25—25 of FIG. 24.

In FIGS. 24 and 25, a thirteenth embodiment is illustrated to include a flange structure 200m and a wrist bearing component 56m. The distal side of the flange structure 200m is configured in a manner that is generally identical to the distal side of the flange structure 200k discussed above. The proximal side 900 of the flange structure 200m, however, is defined by a spherical radius 902. In the particular embodiment illustrated, the spherical radius 902 is centered at a point that is disposed along the axis 904 of the connecting portion 210m. Those skilled in the art will appreciate, however, that the center of the spherical radius 902 may be positioned otherwise. The wrist bearing component 56m likewise includes a distal profile 700m that matingly engages the proximal side 900 of the flange structure 200m.

Figure 26:
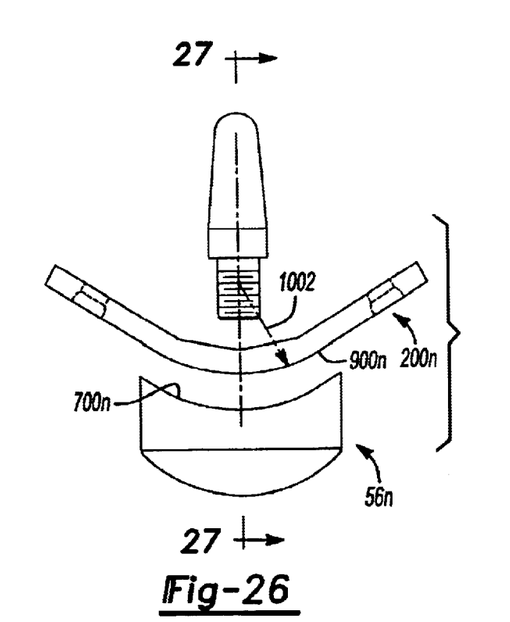
FIG. 26 is an exploded side elevation view of a prosthetic wrist constructed in accordance with the teachings of a fourteenth embodiment of the present invention.
Figure 27:
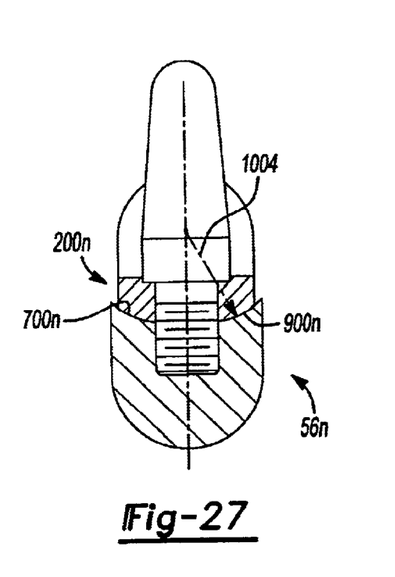
FIG. 27 is a sectional view taken along the line 27—27 of FIG. 26.

In FIGS. 26 and 27, a fourteenth embodiment is illustrated to include a flange structure 200n and a wrist bearing component 56n. The flange structure 200n is generally similar to the flange structure 200m, except that the proximal side 900n is defined by a first radius 1002 in the coronal plane and a second radius 1004 in the sagittal plane. The wrist bearing component 56n is likewise generally similar to the wrist bearing component 56m, except that the distal profile 700n of the wrist bearing component is configured with a first radius in the coronal plane and a second radius in the sagittal plane so as to matingly engage the proximal side 900n of the flange structure 200n.

While some embodiments have been illustrated to include a unitarily formed component, such as a unitarily formed carpal implant, and others have been illustrated to include a component assembly, such as a carpal implant assembly that includes a discretely formed stem and a discretely formed flange structure, those skilled in the art will appreciate that any unitarily formed component may be formed in the alternative utilizing a plurality of discretely formed components and that any embodiment that is shown to be formed using a plurality of discretely formed components may likewise be unitarily formed in the alternative. Accordingly, while the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the foregoing description and the appended claims.

What is claimed is:

1. A prosthetic wrist comprising:
a carpal implant having a body, a lateral flange and a medial flange, the body having an axis that is adapted to extend generally parallel an axis of a capitate bone in a human wrist when the prosthetic wrist is implanted, the lateral flange being coupled to the body and, extending therefrom, the medial flange being coupled to the body and extending therefrom, the lateral flange and the medial flange cooperating to provide the carpal implant with a bone abutment surface having a generally concave shape that is configured to abut a lateral side and a medial side, respectively, of at least a portion of a carpal bone complex of the human wrist.

2. The prosthetic wrist of claim 1, wherein the body includes an interconnecting flange that is coupled to the lateral flange, the interconnecting flange having an interconnecting bone abutment surface that is configured to abut a proximal side of the capitate bone, at least a portion of the interconnecting flange being skewed to the axis of the body by an angle of less than 90 degrees, at least a portion of the interconnecting bone abutment surface also being skewed to the lateral bone abutment surface.

3. The prosthetic wrist of claim 2, wherein the interconnecting flange includes first portion and a second portion each of the first and second portions including a bone abutment surface that is configured to abut a proximal side of the capitate bone, the first portion being coupled to the lateral flange, the second portion being coupled to the medial flange, wherein the bone abutment surface of the second portion is skewed to the lateral flange, and wherein the bone abutment surface of the first portion is skewed to the bone abutment surface of the second portion.

4. The prosthetic wrist of claim 3, wherein the bone abutment surface of the first portion of the interconnecting flange is generally co-planar with the lateral bone abutment surface and the bone abutment surface of the second portion of the interconnecting flange is generally co-planar with the medial bone abutment surface.

5. The prosthetic wrist of claim 3, further comprising a wrist bearing component and a discrete stem, the wrist bearing component being configured to matingly engage a proximal portion of the carpal implant, the stem being configured to extend through an aperture in the interconnecting flange and fixedly engage the wrist bearing component.

6. The prosthetic wrist of claim 2, wherein the lateral bone abutment surface is skewed to the axis of the body by an angle of about 50 degrees.

7. The prosthetic wrist of claim 6, wherein the interconnecting bone abutment surface is skewed relative to the axis of the body by an angle of about 80 degrees.

8. The prosthetic wrist of claim 1, wherein each of the lateral and medial flanges includes a bone screw aperture for receiving therethrough a bone screw that attaches the carpal implant to a distal portion of the human wrist.

9. The prosthetic wrist of claim 1, further comprising a wrist bearing component, the wrist bearing component being coupled to a proximal stem formed on the body of the carpal implant and configured to cooperate in transmitting load through the human wrist.

10. The prosthetic wrist of claim 9, wherein the wrist bearing component is rotatable relative to the carpal implant to permit the wrist bearing component to be positioned a desired installation orientation relative to the carpal implant.

11. The prosthetic wrist of claim 9, wherein the wrist bearing component includes a wrist bearing surface that is defined by a first radius in the coronal plane and a second, different radius in the sagittal plane.

12. The prosthetic wrist of claim 11, wherein the first radius is larger than the second radius.

13. The prosthetic wrist of claim 11, further comprising an alignment device coupled to at least one of the carpal implant and the wrist bearing component, the alignment device being operable for radially fixing the carpal implant and the wrist bearing component at an installation orientation.

14. The prosthetic wrist of claim 13, wherein the alignment device includes a member that may be coupled to one of the carnal implant and the wrist bearing component at several predetermined locations so that the installation orientation may be selected from a plurality of predetermined orientations.

15. The prosthetic wrist of claim 14, wherein the alignment device includes a coupling member that is coupled to one of the carpal implant and the wrist bearing component and a plurality of holes formed in the other one of the carpal implant and the wrist bearing component, the coupling member engaging one of the plurality of holes to thereby align the wrist bearing component relative to the carpal implant.

16. The prosthetic wrist of claim 15, wherein the coupling member is a pin and each hole has a centerline that is circumferentially spaced apart from the centerline of each other hole.

17. The prosthetic wrist of claim 13, wherein the alignment device includes an adhesive material that bonds the wrist bearing component to the proximal stem, the adhesive material operably securing the wrist bearing component to the proximal stem at the installation orientation.

18. The prosthetic wrist of claim 9, wherein the wrist bearing component has a generally arcuate distal profile that is configured to matingly engage a proximal surface of the carpal implant.

19. The prosthetic wrist of claim 18, wherein the wrist bearing component includes an anterior side wall and a posterior side wall that are configured to abut an anterior side and a posterior side, respectively, of the carpal implant.

20. The prosthetic wrist of claim 18, wherein the generally arcuate profile of the wrist bearing component is defined in at least one of a coronal plane and a sagittal plane by a radius.

21. The prosthetic wrist of claim 20, wherein the radius is a spherical radius.

22. The prosthetic wrist of claim 20, wherein the generally arcuate profile of the wrist bearing component is defined by a first radius in the a coronal plane and a second radius in the sagittal plane, the second radius being different than the first radius.

23. The prosthetic wrist of claim 18, wherein the proximal surface of the carpal implant is generally parallel to the bone abutment surface of the carpal implant.

24. The prosthetic wrist of claim 18, wherein at least a portion of the wrist bearing component abuts at least a portion of the proximal surface of at least one of the lateral flange and the medial flange.

25. The prosthetic wrist of claim 9, wherein at least a portion of the proximal surface is generally perpendicular to the axis of the body when the carpal implant is secured to the wrist bearing component.

26. The prosthetic wrist of claim 9, wherein an axis of the proximal stem is offset from the axis of the body in at least one of a lateral or medial direction.

27. The prosthetic wrist of claim 1, wherein the body includes a discrete stem and the lateral and medial flanges are unitarily formed onto a discrete flange structure.

28. The prosthetic wrist of claim 27, wherein the flange structure further includes an interconnecting portion, the interconnecting portion having an interconnecting bone abutment surface that further defines the generally concave shape of the bone abutment surface.

29. The prosthetic wrist of claim 27, further comprising a wrist bearing component that is configured to abut a proximal side of the flange structure, the wrist bearing component including an anti-rotation feature that is configured to cooperate with at least one of the stem and the flange structure to inhibit the wrist bearing component from rotating relative to the flange structure.

30. The prosthetic wrist of claim 29, wherein the anti-rotation feature includes at least one tab, the at least one tab being configured to abut one of the lateral and medial flanges.

31. The prosthetic wrist of claim 27, wherein the stem includes a driving portion, the driving portion being configured to matingly engage a tool to permit the stem to be rotated relative to the flange structure.

32. The prosthetic wrist of claim 1, wherein the body further comprises an interconnecting portion disposed between the lateral and medial flanges, the interconnecting portion having an interconnecting bone abutment surface is arcuately shaped.

33. The prosthetic wrist of claim 32, wherein the lateral bone abutment surface and the medial bone abutment surface are tangent to the interconnecting bone abutment surface.

34. The prosthetic wrist of claim 1, further comprising a wrist bearing component that is fixedly coupled to the carpal implant, the wrist bearing component and the carpal implant being unitarily formed.

35. A prosthetic wrist comprising:
   a carpal implant that is adapted to be implanted in at least a portion of a carpal bone complex of a human wrist;
   a wrist bearing component that is configured to be coupled to the carpal implant;
   wherein the carpal implant includes a flange means with a lateral side and a medial side, the flange means being configured to be disposed between the portion of the carpal bone complex and the wrist bearing component such that the lateral side of the flange means extends about a lateral side of the portion of the carpal bone complex and the medial side of the flange means extends about a medial side of the portion of the carpal bone complex, each of the lateral and medial sides defining a bone abutment surface that extends outwardly away from the bearing and forwardly toward a distal end of the portion of the carpal bone complex.

36. The prosthetic wrist of claim 35, wherein the carpal implant further comprises a discrete stem, the stem being configured to extend through the flange means and engage the wrist bearing component.

37. The prosthetic wrist of claim 36, wherein the stem is releasably engaged to the wrist bearing component.

38. The prosthetic wrist of claim 35, wherein the carpal implant is unitarily formed.

39. The prosthetic wrist of claim 38, wherein the carpal implant and the wrist bearing component are unitarily formed.

* * * * *

UNITED STATES PATENT AND TRADEMARK OFFICE
CERTIFICATE OF CORRECTION

PATENT NO. : 6,746,486 B1
DATED : June 8, 2004
INVENTOR(S) : Shultz et al.

It is certified that error appears in the above-identified patent and that said Letters Patent is hereby corrected as shown below:

Column 3,
Line 32, "a" should be -- an --.

Column 10,
Line 59, "angles" should be -- angled --.

Column 11,
Line 1, "identifically", should be -- identical --.

Column 13,
Line 9, "carnal" should be -- carpal --.
Line 46, delete 2nd occurrence of "a".

Signed and Sealed this

Twenty-fifth Day of January, 2005

JON W. DUDAS
*Director of the United States Patent and Trademark Office*